(12) United States Patent
Tischler

(10) Patent No.: US 7,637,939 B2
(45) Date of Patent: Dec. 29, 2009

(54) HYBRID STENT

(75) Inventor: Brian Tischler, New Brighton, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 261 days.

(21) Appl. No.: 11/172,158

(22) Filed: Jun. 30, 2005

(65) Prior Publication Data

US 2007/0005126 A1   Jan. 4, 2007

(51) Int. Cl.
  *A61F 2/06* (2006.01)
(52) U.S. Cl. ............... 623/1.22; 623/1.15; 623/1.16
(58) Field of Classification Search ........... 623/1.22, 623/1.15, 1.23; 606/191, 192, 194, 196; *A61F 2/06*
  See application file for complete search history.

(56) References Cited

U.S. PATENT DOCUMENTS

| | | | |
|---|---|---|---|
| 5,549,663 A | 8/1996 | Cottone, Jr. ............... 623/1 |
| 5,824,052 A | 10/1998 | Khosravi et al. ........... 623/1 |
| 5,824,053 A | 10/1998 | Khosravi et al. ........... 623/1 |
| 5,879,395 A * | 3/1999 | Tornier et al. ........... 623/20.13 |
| 5,925,061 A | 7/1999 | Ogi et al. |
| 6,042,597 A | 3/2000 | Kveen et al. ............. 606/198 |
| 6,319,277 B1 * | 11/2001 | Rudnick et al. ........... 623/1.13 |
| 6,352,552 B1 | 3/2002 | Levinson et al. .......... 623/1.15 |
| 6,355,059 B1 | 3/2002 | Richter et al. |
| 6,375,677 B1 * | 4/2002 | Penn et al. ............... 623/1.16 |
| 6,423,091 B1 | 7/2002 | Hojeibane |
| 6,425,915 B1 | 7/2002 | Khosravi et al. .......... 623/1.22 |
| 6,488,703 B1 | 12/2002 | Kveen et al. |
| 6,503,270 B1 | 1/2003 | Richter et al. ........... 623/1.15 |
| 6,532,552 B1 | 3/2003 | Benignus et al. |
| 6,551,351 B2 | 4/2003 | Smith et al. |
| 6,736,844 B1 | 5/2004 | Glatt et al. ............... 623/1.22 |
| 6,878,162 B2 | 4/2005 | Bales et al. .............. 623/1.15 |
| 6,896,696 B2 * | 5/2005 | Doran et al. ............. 623/1.15 |
| 6,969,402 B2 | 11/2005 | Bales et al. ............. 623/1.15 |
| 7,004,968 B2 * | 2/2006 | Lootz et al. ............. 623/1.15 |
| 7,169,175 B2 | 1/2007 | Cottone, Jr. et al. |
| 2002/0111669 A1 * | 8/2002 | Pazienza et al. ........... 623/1.15 |
| 2003/0055489 A1 * | 3/2003 | Kveen et al. ............. 623/1.15 |
| 2004/0002750 A1 * | 1/2004 | Majercak ................. 623/1.11 |
| 2004/0002753 A1 * | 1/2004 | Burgermeister et al. .... 623/1.15 |
| 2004/0034402 A1 | 2/2004 | Bales et al. ............... 623/1.2 |
| 2004/0044401 A1 | 3/2004 | Bales et al. .............. 623/1.22 |

(Continued)

FOREIGN PATENT DOCUMENTS

EP   0 890 346 A1   1/1999

(Continued)

*Primary Examiner*—Eduardo C Robert
*Assistant Examiner*—Jason-Dennis Stewart
(74) *Attorney, Agent, or Firm*—Vidas, Arrett & Steinkraus P.A.

(57) ABSTRACT

A stent comprises at least one segment. The segment comprises a first tubular closed ring section, a second tubular closed ring section, a first generally helical section having a first end and a second end, and a second generally helical section having a first end and a second end. The first ends of the first and second generally helical sections extend from the first tubular closed ring section and the second ends extend from the second tubular closed ring section. The first and second generally helical sections both extend in the same direction about the longitudinal axis of the stent.

5 Claims, 22 Drawing Sheets

U.S. PATENT DOCUMENTS

| | | | |
|---|---|---|---|
| 2004/0122504 A1 | 6/2004 | Hogendijk | 623/1.15 |
| 2004/0143318 A1* | 7/2004 | Tseng et al. | 623/1.16 |
| 2004/0158314 A1 | 8/2004 | Hogendijk | 623/1.15 |
| 2004/0172126 A1* | 9/2004 | Hojeibane | 623/1.15 |
| 2004/0186556 A1 | 9/2004 | Hogendijk et al. | 623/1.16 |
| 2004/0236405 A1* | 11/2004 | Kula et al. | 623/1.15 |
| 2005/0033410 A1 | 2/2005 | Hogendijk et al. | 623/1.15 |
| 2005/0165469 A1 | 7/2005 | Hogendijk | 623/1.15 |
| 2006/0004438 A1 | 1/2006 | Alexander et al. | 623/1.22 |
| 2006/0030934 A1 | 2/2006 | Hogendijk et al. | 623/1.22 |
| 2007/0208409 A1* | 9/2007 | Quigley | 623/1.13 |
| 2007/0219618 A1* | 9/2007 | Cully et al. | 623/1.13 |

FOREIGN PATENT DOCUMENTS

| | | |
|---|---|---|
| EP | 0945107 | 9/1999 |
| WO | WO 98/38945 | 9/1998 |
| WO | WO 03/086237 | 10/2003 |

\* cited by examiner

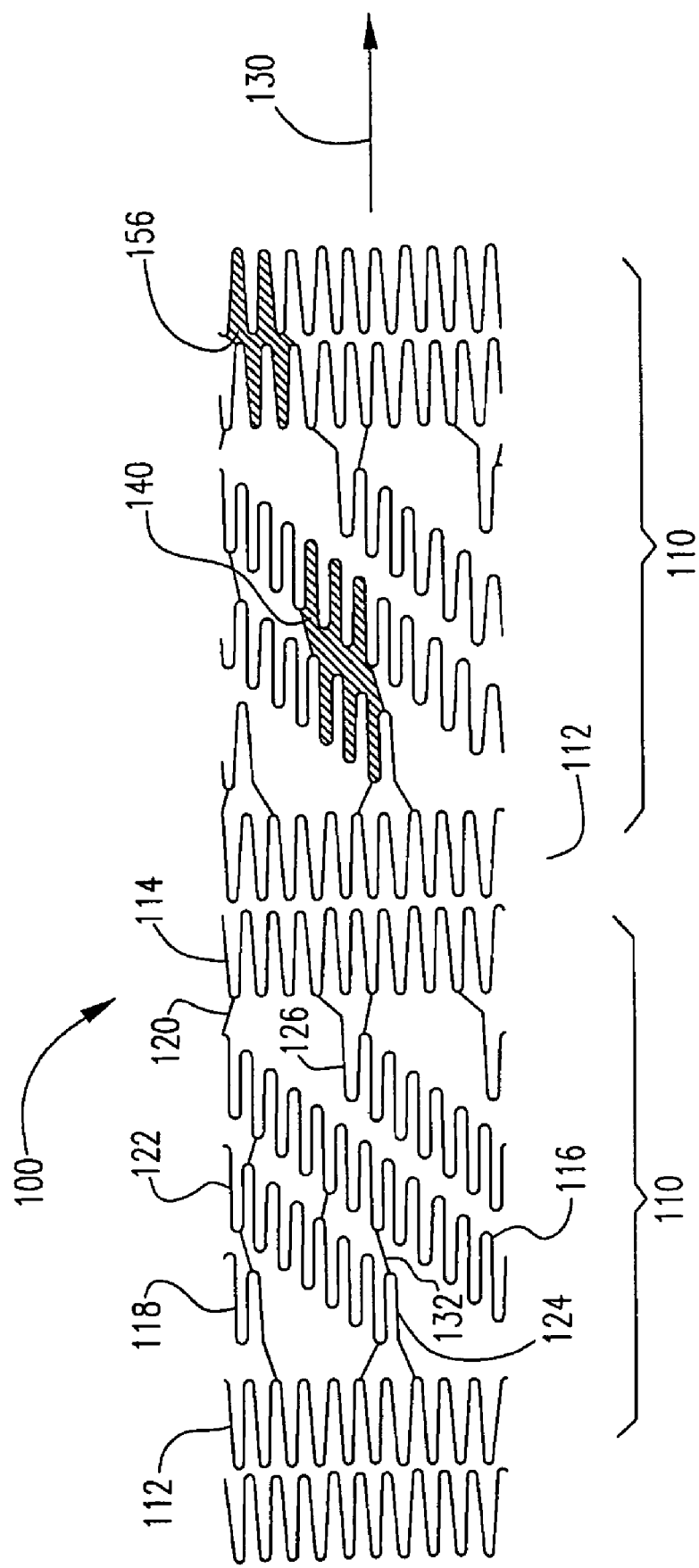

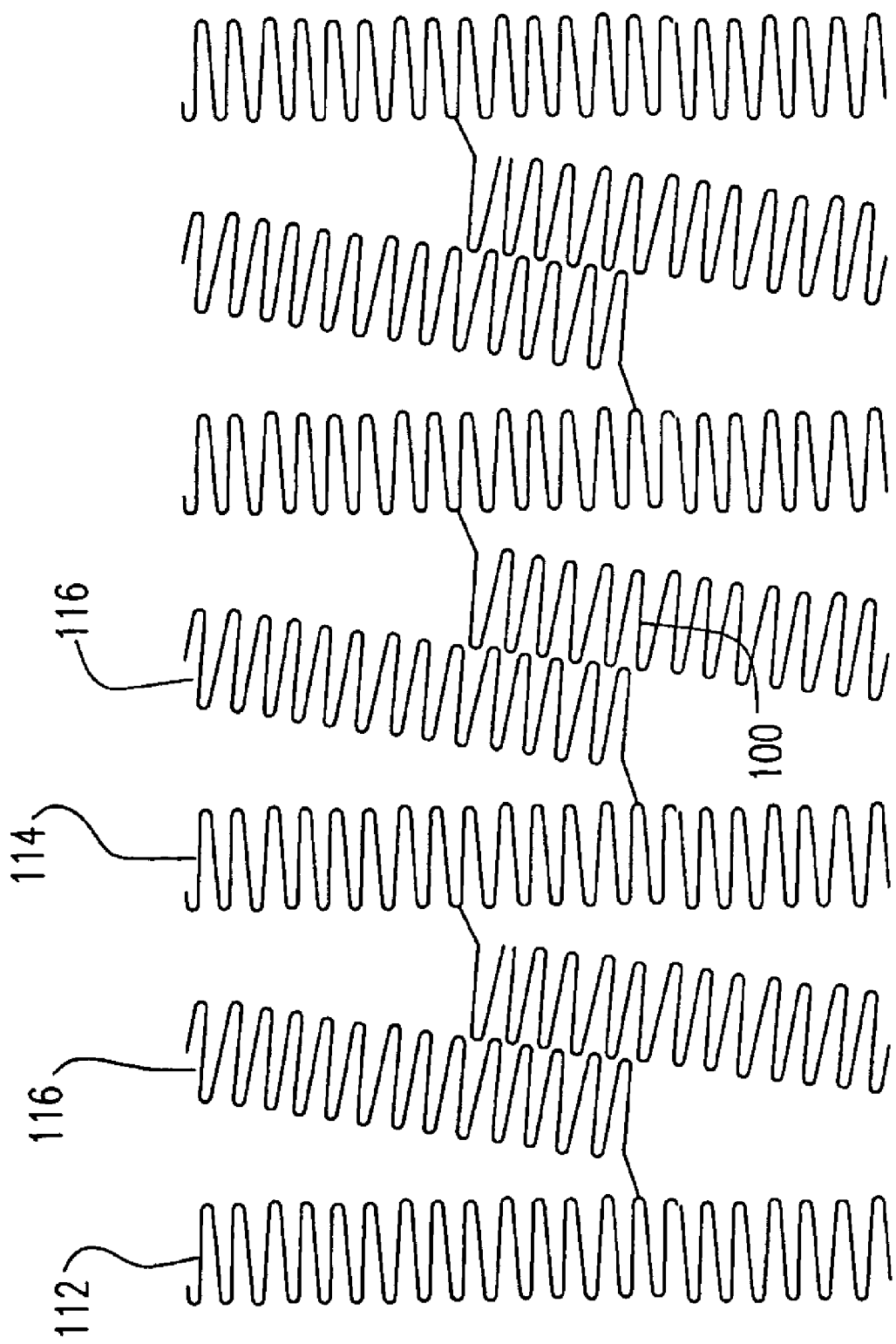

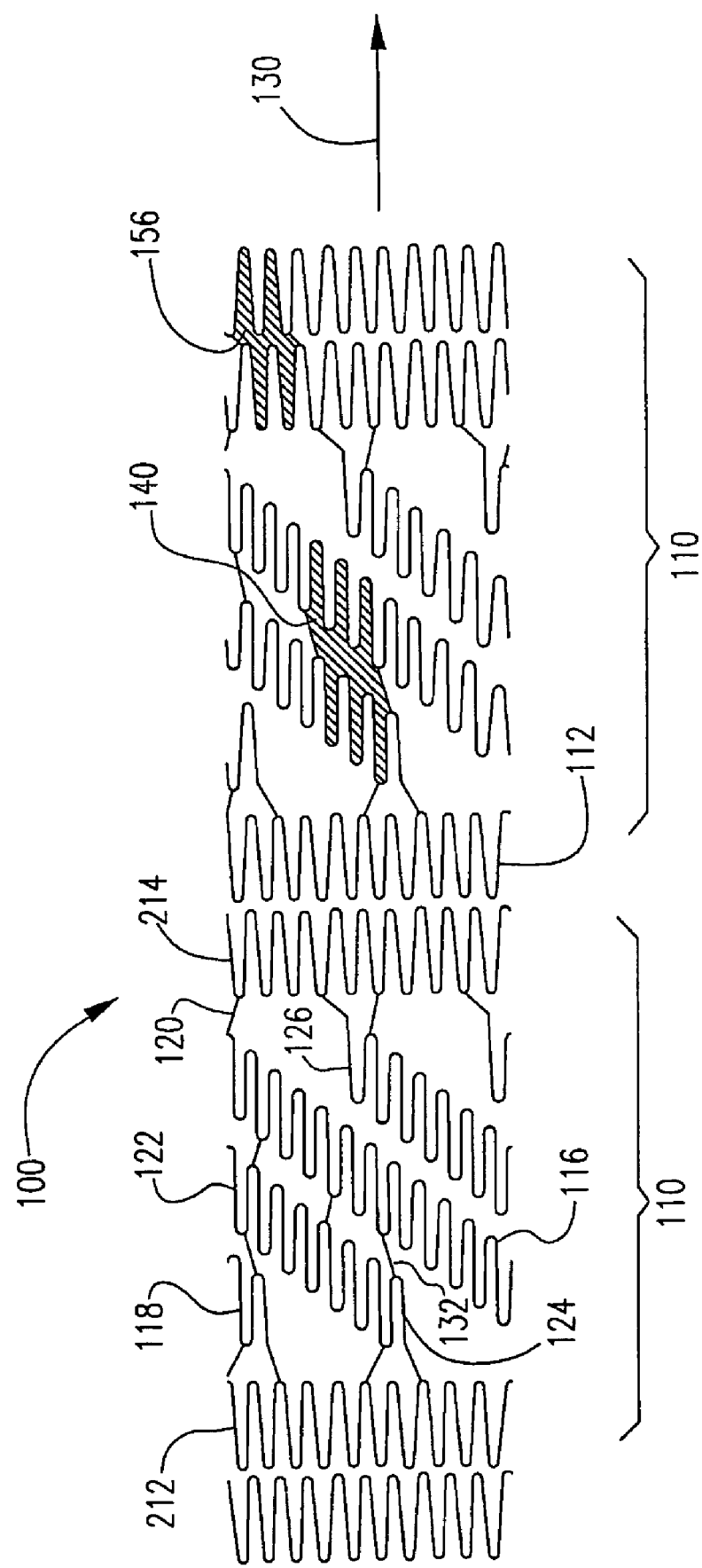

_US 7,637,939 B2_

HYBRID STENT

BACKGROUND OF THE INVENTION

1. Field of the Invention

In some embodiments this invention relates to implantable medical devices, their manufacture, and methods of use. Some embodiments are directed to delivery systems, such as catheter systems of all types, which are utilized in the delivery of such devices.

2. Description of the Related Art

A stent is a medical device introduced to a body lumen and is well known in the art. Typically, a stent is implanted in a blood vessel at the site of a stenosis or aneurysm endoluminally, i.e. by so-called "minimally invasive techniques" in which the stent in a radially reduced configuration, optionally restrained in a radially compressed configuration by a sheath and/or catheter, is delivered by a stent delivery system or "introducer" to the site where it is required. The introducer may enter the body from an access location outside the body, such as through the patient's skin, or by a "cut down" technique in which the entry blood vessel is exposed by minor surgical means.

Stents, grafts, stent-grafts, vena cava filters, expandable frameworks, and similar implantable medical devices, collectively referred to hereinafter as stents, are radially expandable endoprostheses which are typically intravascular implants capable of being implanted transluminally and enlarged radially after being introduced percutaneously.

Stents may be self-expanding, expanded by an internal radial force, such as when mounted on a balloon, or a combination of self-expanding and balloon expandable (hybrid expandable).

Stents may be created by methods including cutting or etching a design from a tubular stock, from a flat sheet which is cut or etched and which is subsequently rolled or from one or more interwoven wires or braids.

Stents may be implanted in a variety of body lumens or vessels such as within the vascular system, urinary tracts, bile ducts, fallopian tubes, coronary vessels, secondary vessels, etc. Stents may be used to reinforce body vessels and to prevent restenosis following angioplasty in the vascular system.

It is in particular desirable to have a stent which may be used in the superficial femoral artery (SFA) or in other vessels where high axial and bending compliance is required. SFA vessels are known for their high degree of elasticity and motion including axial compression/stretch, bend, kink, twist and flattening. It is desired that a stent implant have similar properties mechanically to the vessel in which it is implanted while still maintaining sufficient radial force to keep the vessel propped open. Fractures have been observed in the femoral-popliteal artery beds for a number of commercial Nitinol self-expanding stents which rely on a stiff metallic connector to connect adjacent radial serpentine segments. Axial or bending force is transmitted through these connectors to the serpentine rings since the connectors cannot significantly bend to accommodate the change in stent shape.

Typically, designing the stent's serpentine rings to be more flexible creates more axial or bending compliant stents, but results in a tradeoff in radial expansion force. De-coupling radial force with axial compliance would be desirable.

The art referred to and/or described above is not intended to constitute an admission that any patent, publication or other information referred to herein is "prior art" with respect to this invention. In addition, this section should not be construed to mean that a search has been made or that no other pertinent information as defined in 37 C.F.R. §1.56(a) exists.

All US patents and applications and all other published documents mentioned anywhere in this application are incorporated herein by reference in their entirety.

Without limiting the scope of the invention a brief summary of some of the claimed embodiments of the invention is set forth below. Additional details of the summarized embodiments of the invention and/or additional embodiments of the invention may be found in the Detailed Description of the Invention below.

A brief abstract of the technical disclosure in the specification is provided as well only for the purposes of complying with 37 C.F.R. 1.72. The abstract is not intended to be used for interpreting the scope of the claims.

BRIEF SUMMARY OF THE INVENTION

This invention contemplates a number of embodiments where any one, any combination of some, or all of the embodiments can be incorporated into a stent and/or a stent delivery system and/or a method of use.

At least one embodiment of the invention is directed to a stent comprising at least two closed ring sections interconnected by at least two generally helical sections in which the generally helical sections are configured in either a clockwise or counterclockwise direction relative to the longitudinal axis of the stent.

At least one embodiment of the invention is directed to a stent comprising at least two closed ring sections interconnected by at least two generally helical sections in which at least one of the generally helical sections nest within one of the other the generally helical sections.

At least one embodiment of the invention is directed to a stent comprising at least two closed ring sections interconnected by one generally helical section in which at least a portion of the generally helical section nest within another portion of the generally helical section.

In at least one embodiment, the invention is directed to a stent comprising at least one segment. The segment comprises a first tubular closed ring section, a second tubular closed ring section, a first generally helical section having a first end and a second end, the first end extending from the first tubular closed ring section, the second end extending from the second tubular closed ring section and a second generally helical section having a first end and a second end, the first end extending from the first tubular closed ring section, the second end extending from the second tubular closed ring section. The first and second generally helical sections both extend in the same direction about the longitudinal axis of the stent.

In some embodiments, the first and second generally helical sections are each in the form of a serpentine band. The first and second generally helical sections may be interconnected to one another at one or more locations, each of the locations being axially displaced from the first and second tubular closed ring sections.

The stent may comprise two or more of the segments, with the segments arranged end to end and adjacent segments connected one to the other.

The first and second generally helical sections may be interconnected at a plurality of locations to define a plurality of cells which are bounded at one end by one of the first and second generally helical sections and bounded at another end by another of the first and second generally helical sections.

In some embodiments, the stent may comprise at least one cell which is bounded at one end by a portion of the first tubular closed ring section and at another end by a portion of the first generally helical section.

In some embodiments, the stent may comprise at least one cell which is bounded at one end by a portion of the first tubular closed ring section and at another end by a portion of the second generally helical section.

In some embodiments, the first and second generally helical sections may both extend in a clockwise direction about the longitudinal axis of the stent or both may extend in a counterclockwise direction. The stent may have at least one segment having clockwise extending generally helical sections and at least one other segment having counter-clockwise extending generally helical sections In some embodiments, the first tubular closed ring section comprises two serpentine bands, each of which forms a closed pathway about the longitudinal axis of the stent and wherein the second tubular closed ring section comprises two serpentine bands, each of which forms a closed pathway about the longitudinal axis of the stent.

In some embodiments, at least one of the first and second tubular closed ring sections includes a serpentine band having struts of different lengths within the band.

In some embodiments, the stent may comprise a plurality of closed ring sections, and a plurality of generally helical portions, each of which includes at least two side-by-side generally helical paths which extend in the same direction about the longitudinal axis of the stent. The plurality of closed ring sections and the plurality of generally helical portions are arranged such that one of the generally helical portions is disposed between two closed ring sections and another of the generally helical portions is disposed between two closed ring sections. The first and second generally helical portions are separated one from the other by at least one closed ring section.

The side-by-side generally helical paths may be connected one to the other in between the closed ring sections.

In some embodiments, the first section is in closed serpentine ring form and the second sections being in generally helical form of helix.

In some of the embodiments, at least one of the closed ring sections includes a serpentine band having peaks and troughs and struts extending therebetween, at least some of the struts being of different length from others of the struts.

In some embodiments, the invention is directed to a stent comprising a plurality of non-helical ring sections and a plurality of generally helical portions, each of which includes at least two side-by-side generally helical paths which extend in the same direction about the longitudinal axis of the stent. The plurality of non-helical ring sections and the plurality of generally helical portions are arranged such that one of the generally helical portions is disposed between two non-helical ring sections and another of the generally helical portions is disposed between two non-helical ring sections. The first and second generally helical portions are separated one from the other by at least one non-helical ring section.

In some embodiments, one or more of the non-helical rings sections are in the form of a closed ring section which forms a closed pathway around a longitudinal axis of the stent.

In some embodiments, one or more of the non-helical ring sections are in the form of an open ring sections.

In some embodiments, at least one non-helical ring section includes a serpentine band having peaks and troughs and struts extending therebetween, at least some of the struts being of different length from others of the struts.

These and other embodiments which characterize the invention are pointed out with particularity in the claims annexed hereto and forming a part hereof. However, for additional understanding of the invention, its advantages and objectives obtained by its use, reference should be made to the drawings which form a further part hereof and the accompanying descriptive matter, in which there is illustrated and described embodiments of the invention.

BRIEF DESCRIPTION OF THE SEVERAL VIEWS OF THE DRAWINGS

A detailed description of the invention is hereafter described with specific reference being made to the drawings.

FIG. 2 is a flat pattern of an inventive stent.

FIG. 5c shows an embodiment of an inventive stent with a nesting generally helical section.

FIG. 6 is a flat pattern of an inventive stent

DETAILED DESCRIPTION OF THE INVENTION

Figure 1:
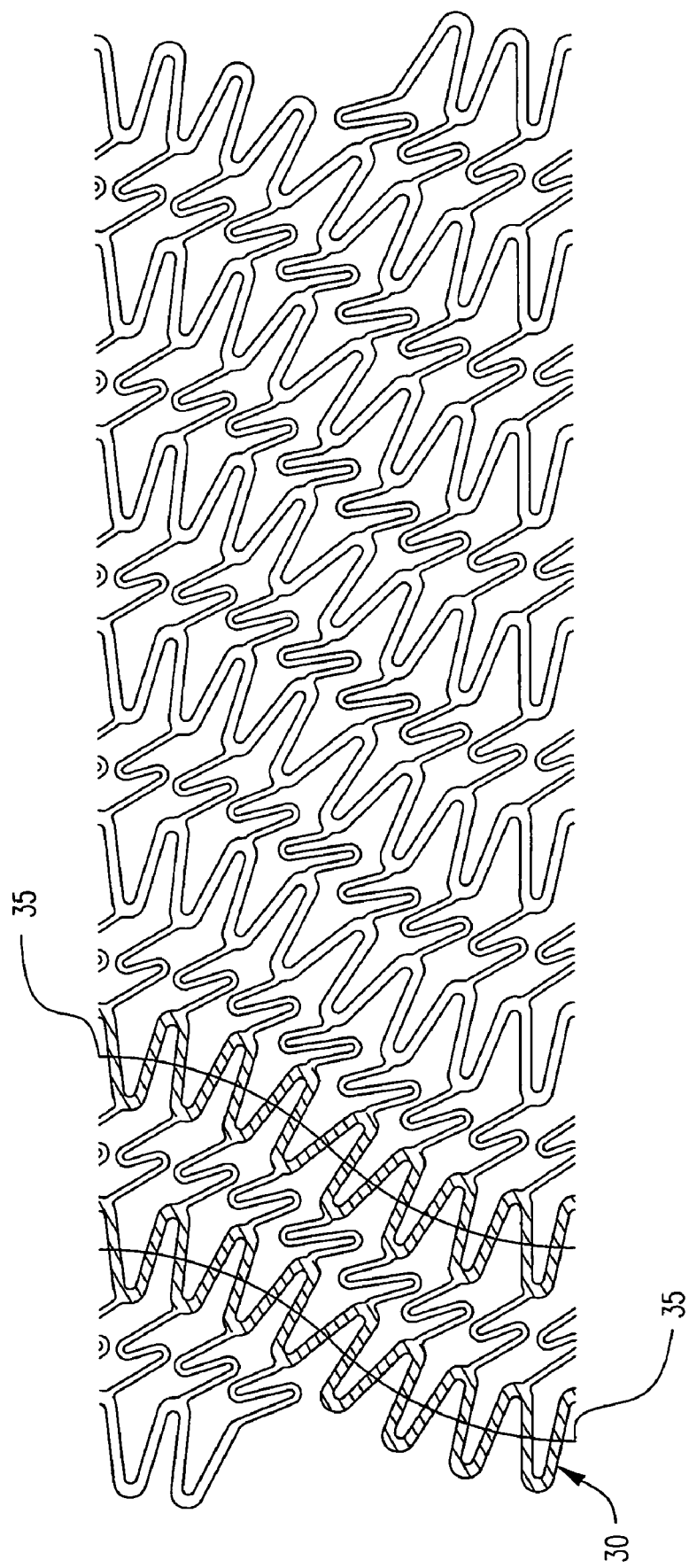
FIG. 1 is a prior art illustration of a stent with generally helical pathways.

While this invention may be embodied in many different forms, there are described in detail herein specific embodiments of the invention. This description is an exemplification of the principles of the invention and is not intended to limit the invention to the particular embodiments illustrated.

For the purposes of this disclosure, like reference numerals in the figures shall refer to like features unless otherwise indicated.

The term generally helical section is intended to encompass sections which are serpentine, but which, nevertheless extend in a substantially helical direction. As shown by way of example, pathway 30, a portion of which is marked by hash marks in FIG. 1, is considered to be generally helical. Although the pathway cuts back and forth relative to the longitudinal axis, centerline 35 of the curve is, nevertheless, generally helical. It is within the scope of the invention for the generally helical sections disclosed herein to have a constant pitch or a non-constant pitch.

The invention is directed to a stent such as that shown at 100 in FIG. 2. Stent 100 comprises at least one segment 110. Segment 110 comprises a first tubular closed ring section 112 and a second tubular closed ring section 114. Segment 110 further comprises a first generally helical section 116 having a first end 118 and a second end 120. First end 118 extends from first tubular closed ring section 112 and second end 120 extends from second tubular closed ring section 114. Segment 110 further comprises a second generally helical section 122 having a first end 124 and a second end 126. First end 124 extends from first tubular closed ring section 112 and second end 126 extends from second tubular closed ring section 114. First and second generally helical sections 116 and 122 both extend in the same direction about the longitudinal axis 130 of the stent.

Desirably, the first and second generally helical sections will each be in the form of a serpentine band. More desirably, as shown in FIG. 2, the first and second generally helical sections will extend in the same direction. Thus, the first and second generally helical sections may extend in a counter-clockwise direction about the longitudinal axis of the stent or they may extend in a clockwise direction about the stent.

The first and second generally helical sections may be interconnected to one another at one or more locations, each of the locations being axially displaced from the first and second tubular closed ring sections. As shown in FIG. 2, by way of example, connectors 132 connect generally helical sections 116 and 122. Connectors 132 in FIG. 1 are linear. More generally, the connectors may be unaligned with the longitudinal axis of the stent, as shown in FIG. 2 or they may be aligned with the longitudinal axis of the stent.

Figure 3A:
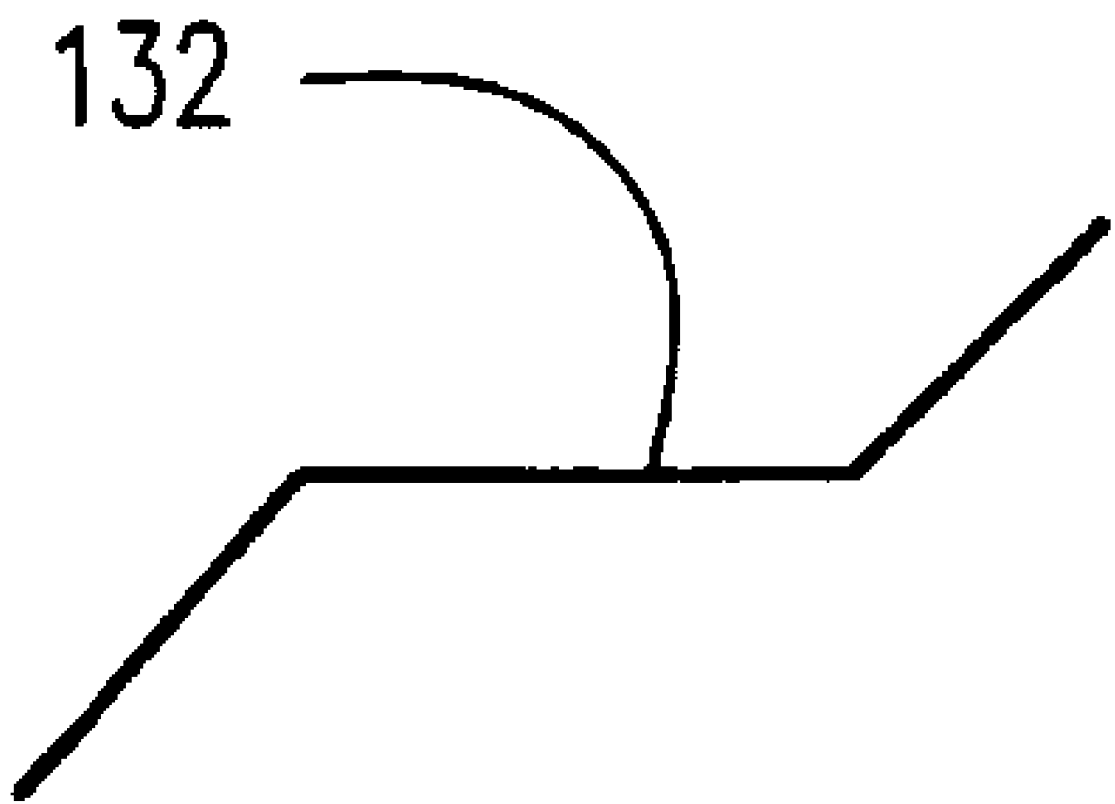
FIG. 3a is a diagonal, stepped connecter with a plurality of linear sections.
Figure 3B:
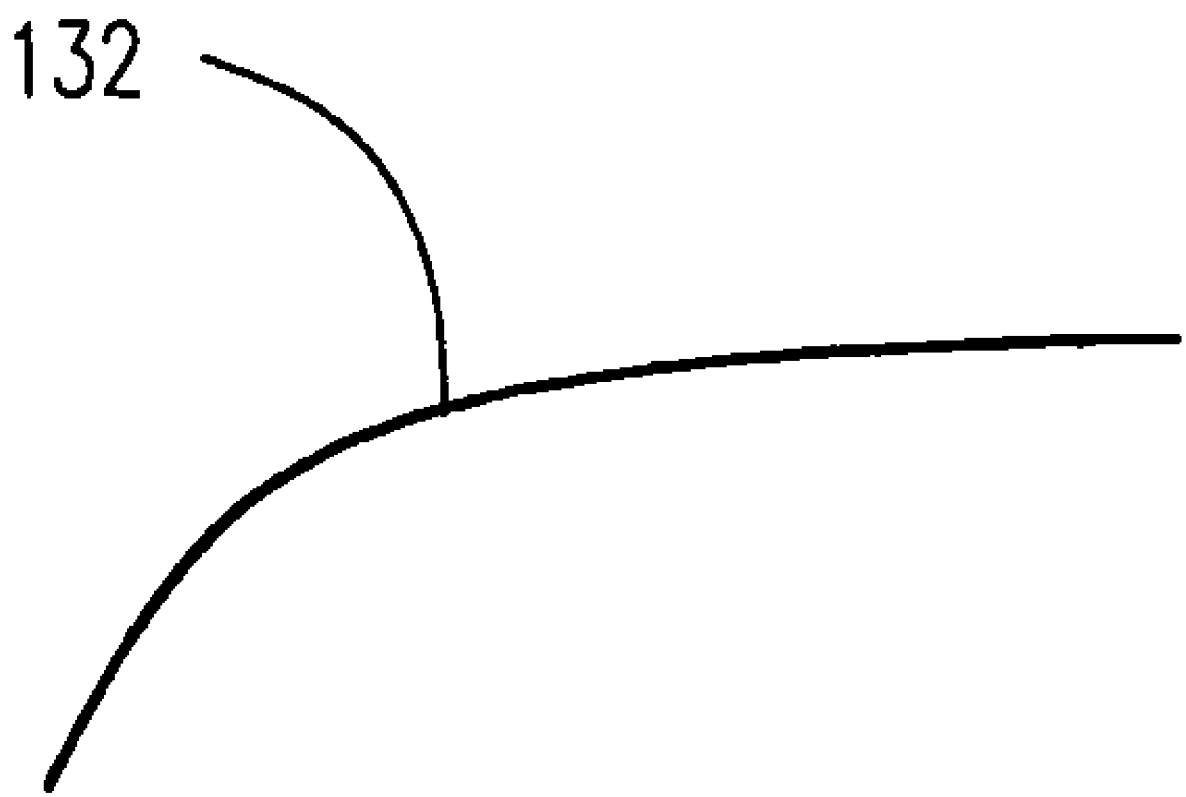
FIG. 3b is a bent connector.
Figure 3C:
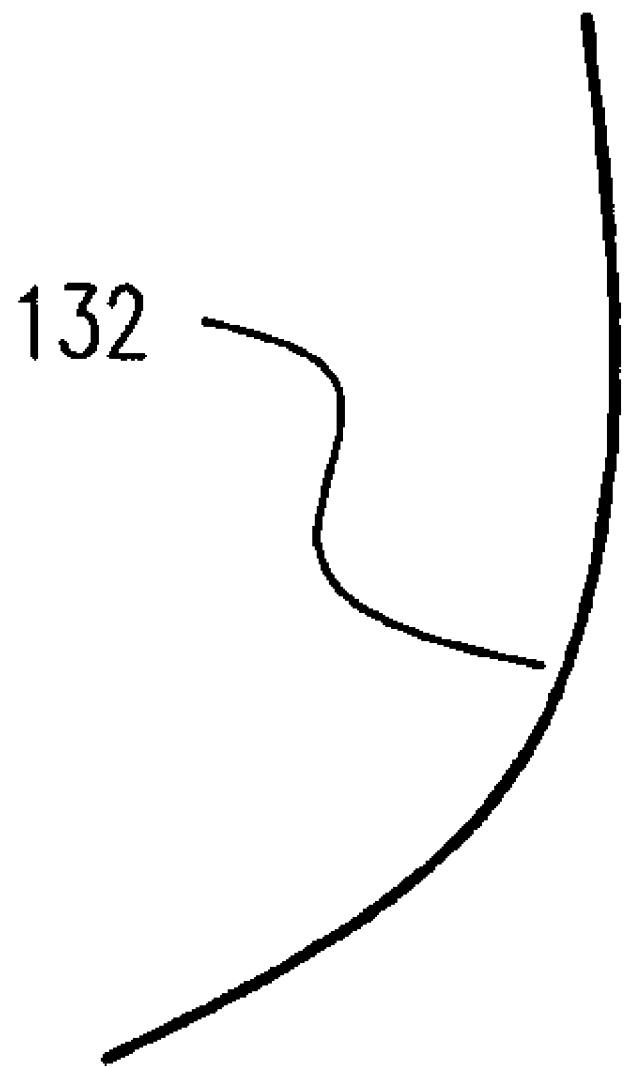
FIG. 3c is a curved connecter.
Figure 3D:
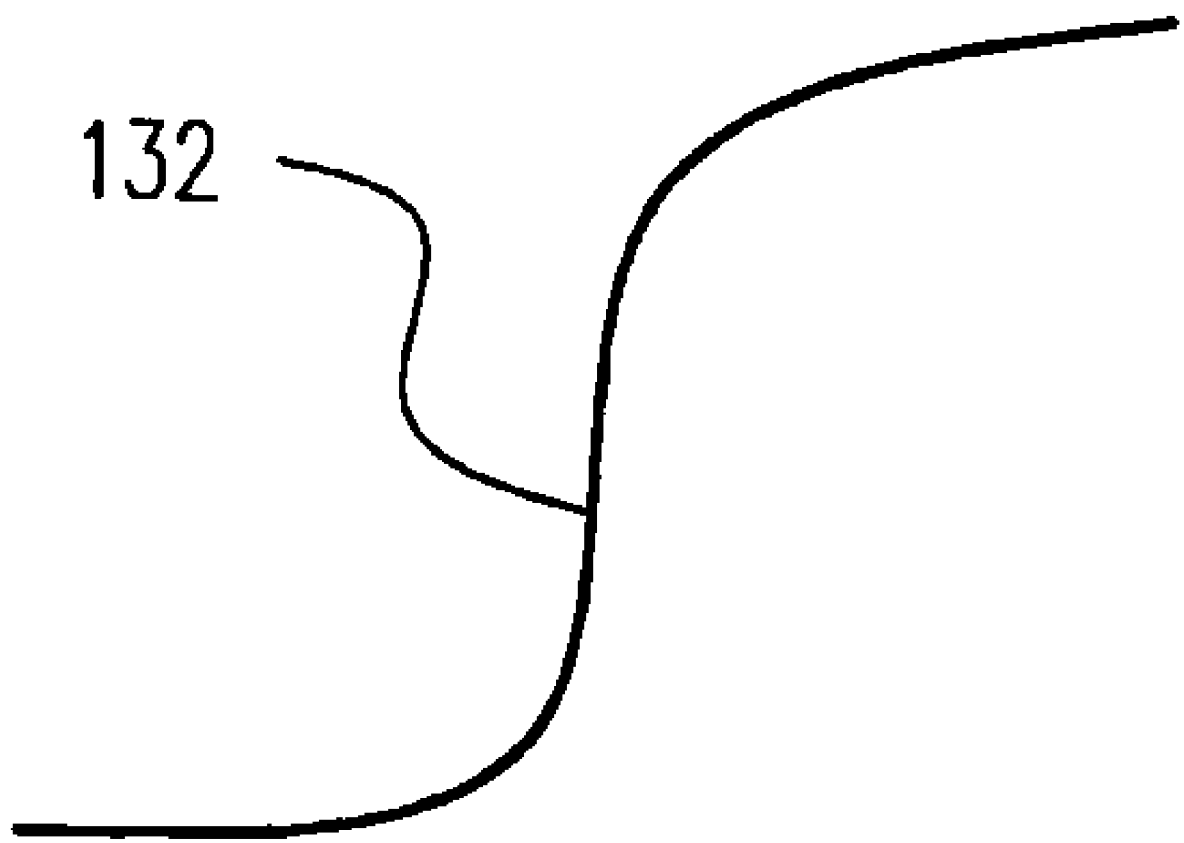
FIG. 3d is an S shaped connecter.
Figure 3E:
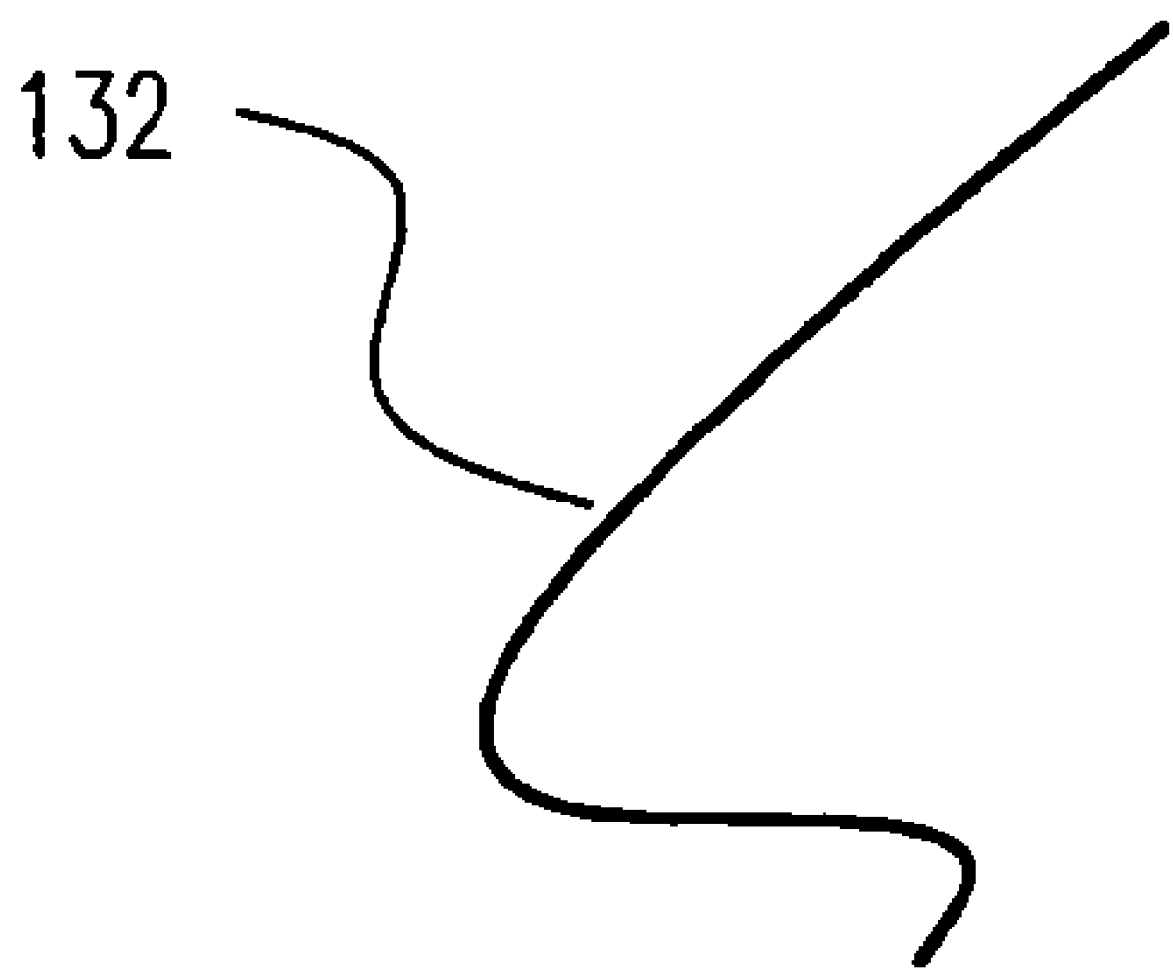
FIG. 3e is another curved connector.
Figure 3F:
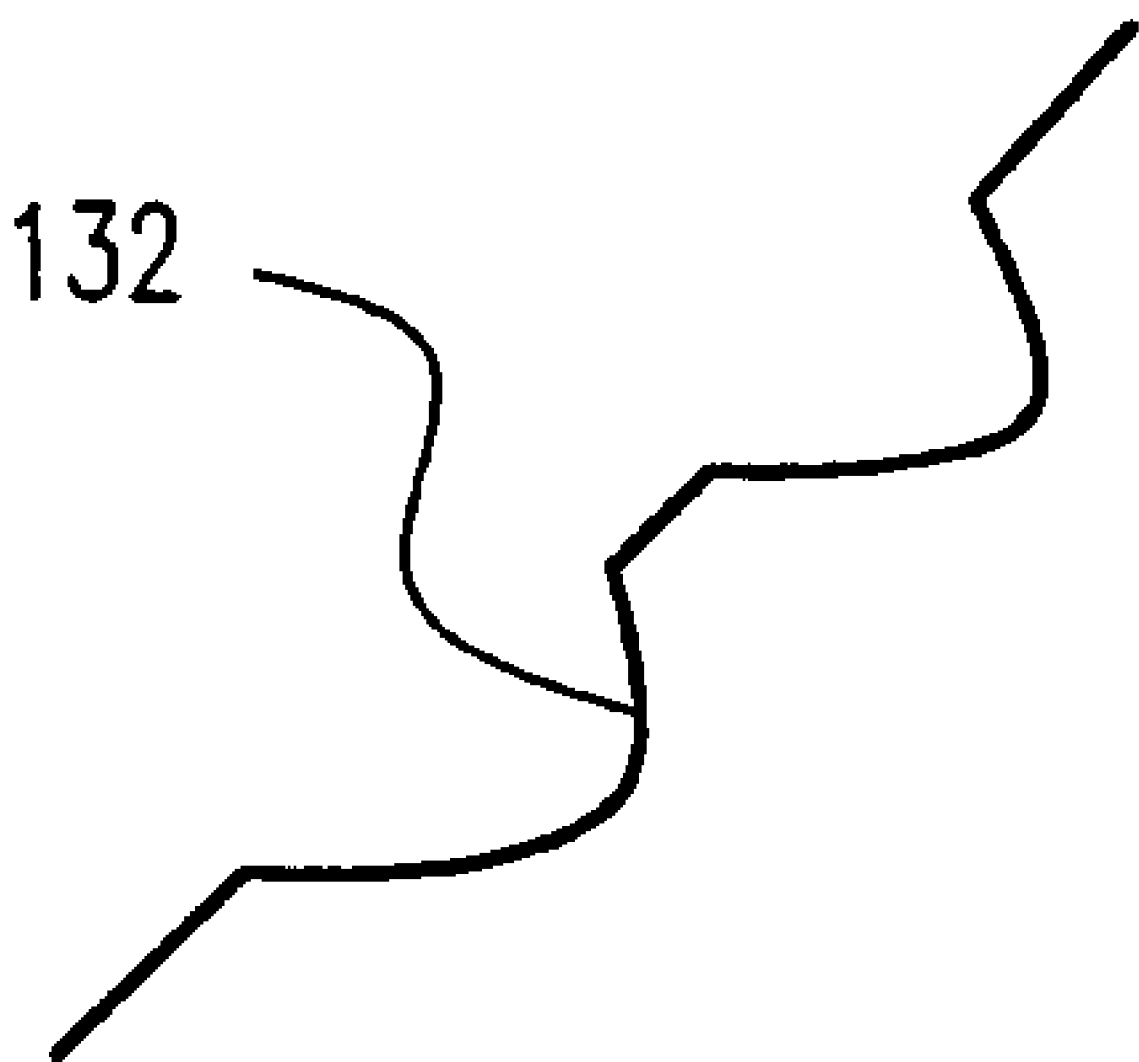
FIG. 3f is a curved connector with a plurality of curved sections that open in the same direction.
Figure 3G:
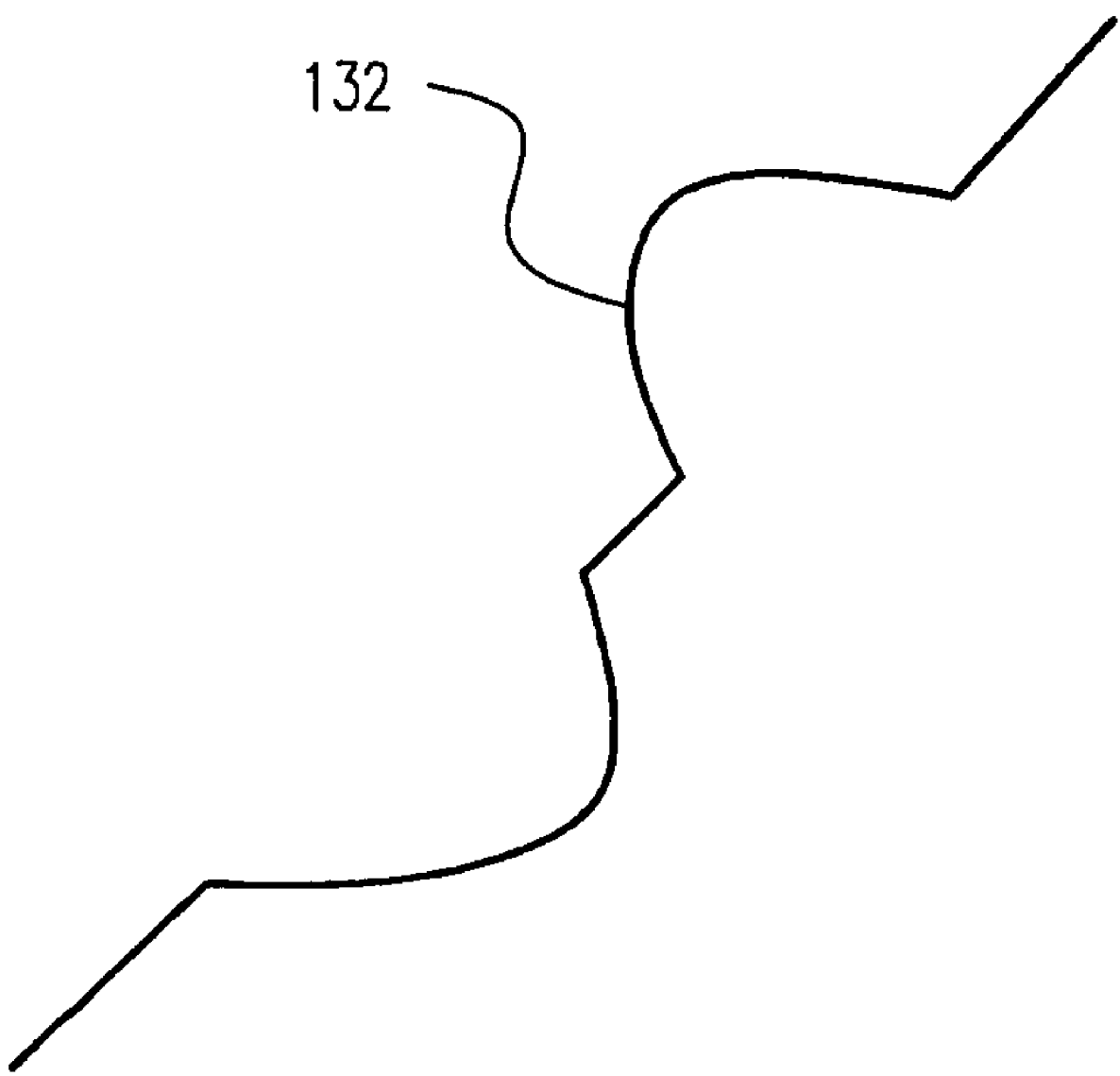
FIG. 3g is a curved connector with curved sections that open in opposing directions.

In the former case, the connectors may be straight or curved, so long as the first and seconds of the connectors are offset from one another circumferentially (i.e. in a circumferentially direction) and longitudinally (i.e. in an axial direction). Curved connectors may include one or more curved sections. The curvature of the curved section(s) may be constant or variable. The connectors may optionally include curved sections as well as one or more straight sections. The connectors may include one or more sections which open in a first direction and one or more sections which open in a second direction which is different from the first direction, as shown by way of example in FIGS. 3d-g. FIGS. 3a, 3b and 3c show a linear connector, a curved connector and another curved connector, respectively.

Figure 4A:
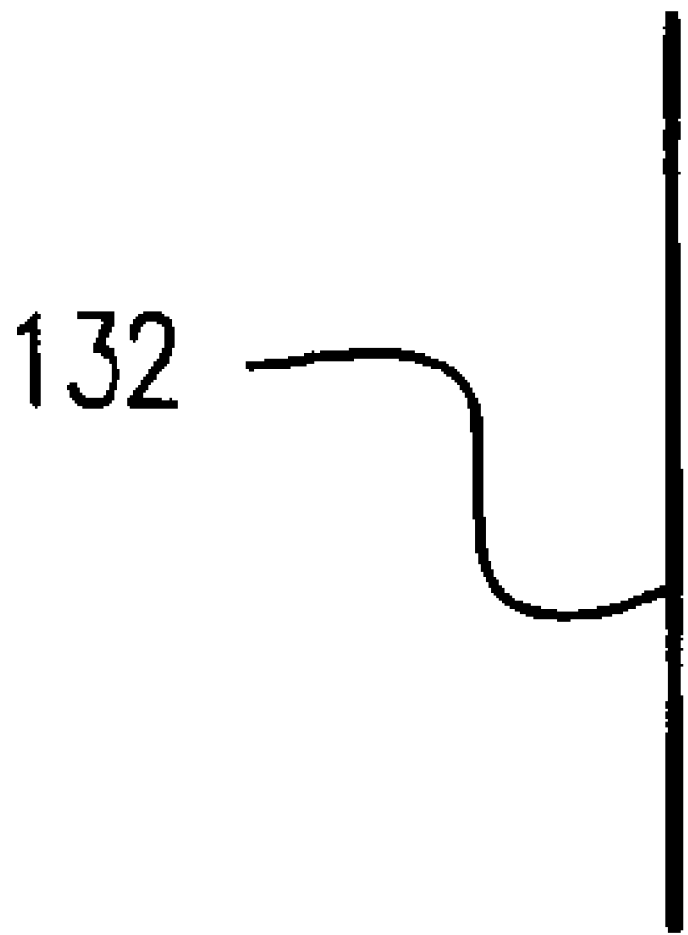
FIG. 4a is a straight peak to trough connecter whose ends are circumferentially aligned.
Figure 4B:
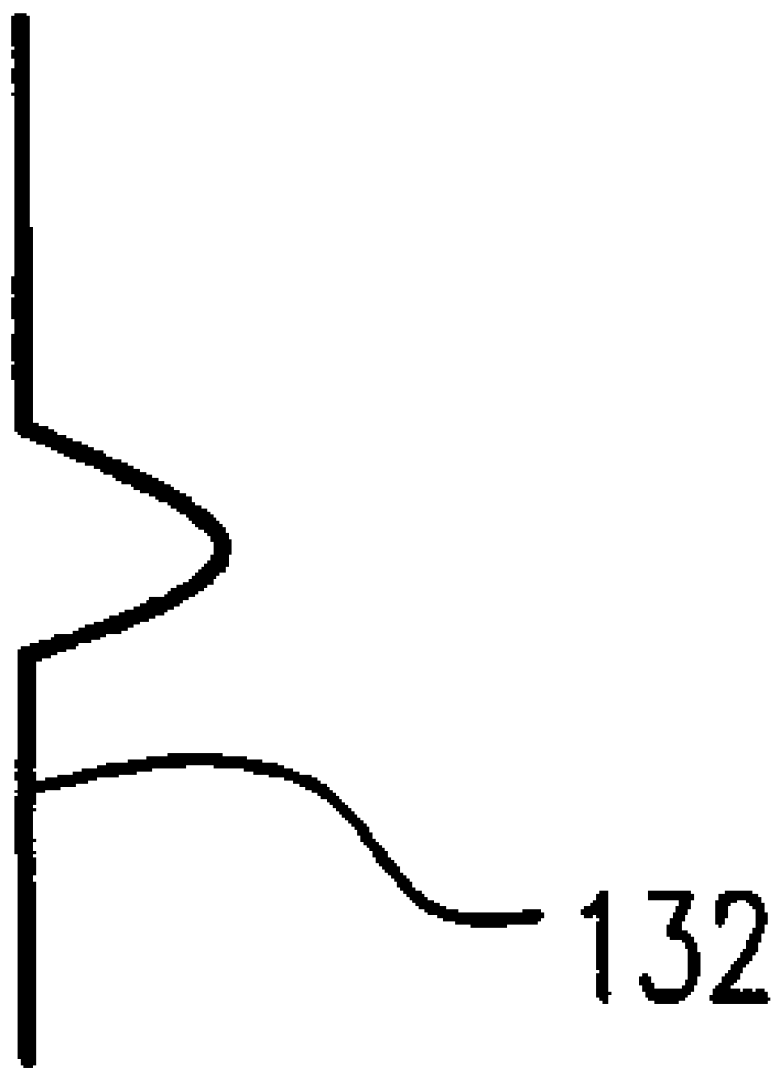
FIG. 4b is a bent peak to trough connecter whose ends are circumferentially aligned.
Figure 4C:
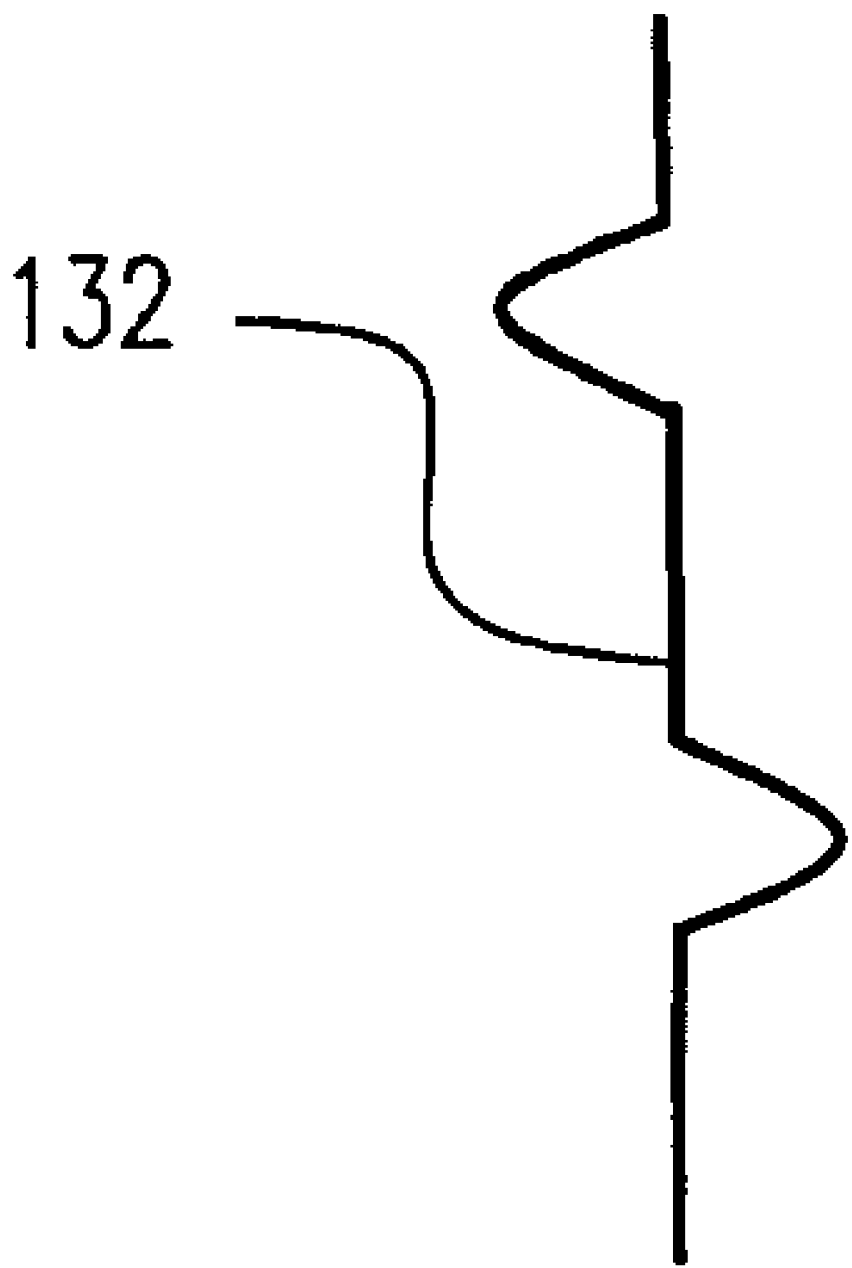
FIG. 4c is a double bend peak to trough connecter whose ends are circumferentially aligned.

In the latter case, the connectors may be straight or curved, so long as the first and seconds of the connectors are aligned with one another in a circumferential direction and offset from one another longitudinally. Curved connectors may include one or more curved sections. The curvature of the curved section(s) may be constant or variable. The connectors may optionally include curved sections as well as one or more straight sections. The connectors may include one or more sections which open in a first direction and one or more sections which open in a second direction which is different from the first direction. Examples of such connectors are shown in FIGS. 4a-4c. One of ordinary skill in the art will also recognize that the connectors of FIGS. 3a-3g may also be suitably modified so that the ends of the connectors are circumferentially aligned but displaced axially.

Figure 5A:
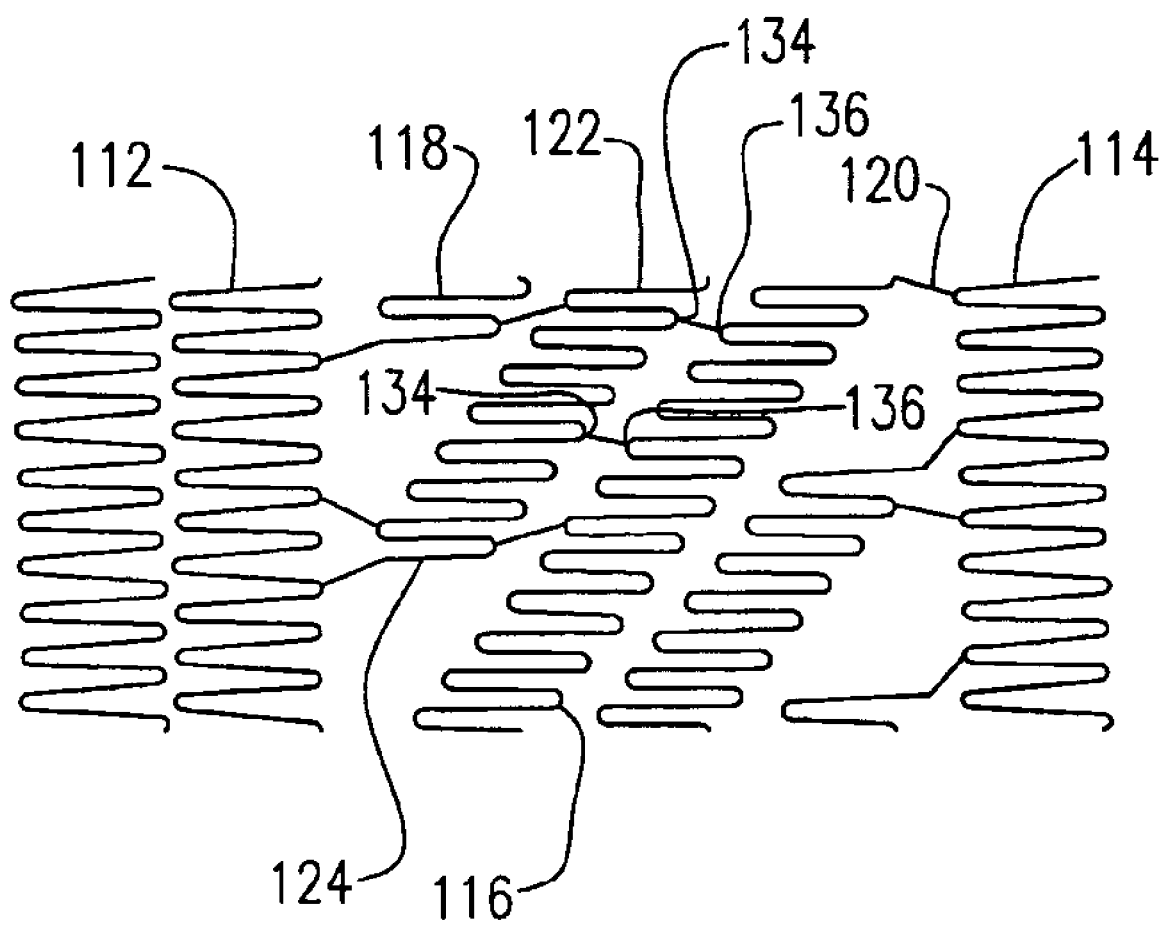
FIG. 5a shows an embodiment of an inventive stent with an overlapping peak and trough.

The first and second generally helical sections may also be interconnected directly to one another at one or more locations from peak to trough. An example of such connectivity is shown in FIG. 5a. Peak 134 overlaps trough 136.

The connectivity between the first and second generally helical sections may include both the connectors shown in FIGS. 3a-3g or FIGS. 4a-4c and the connections shown in FIG. 5a.

Figure 11:
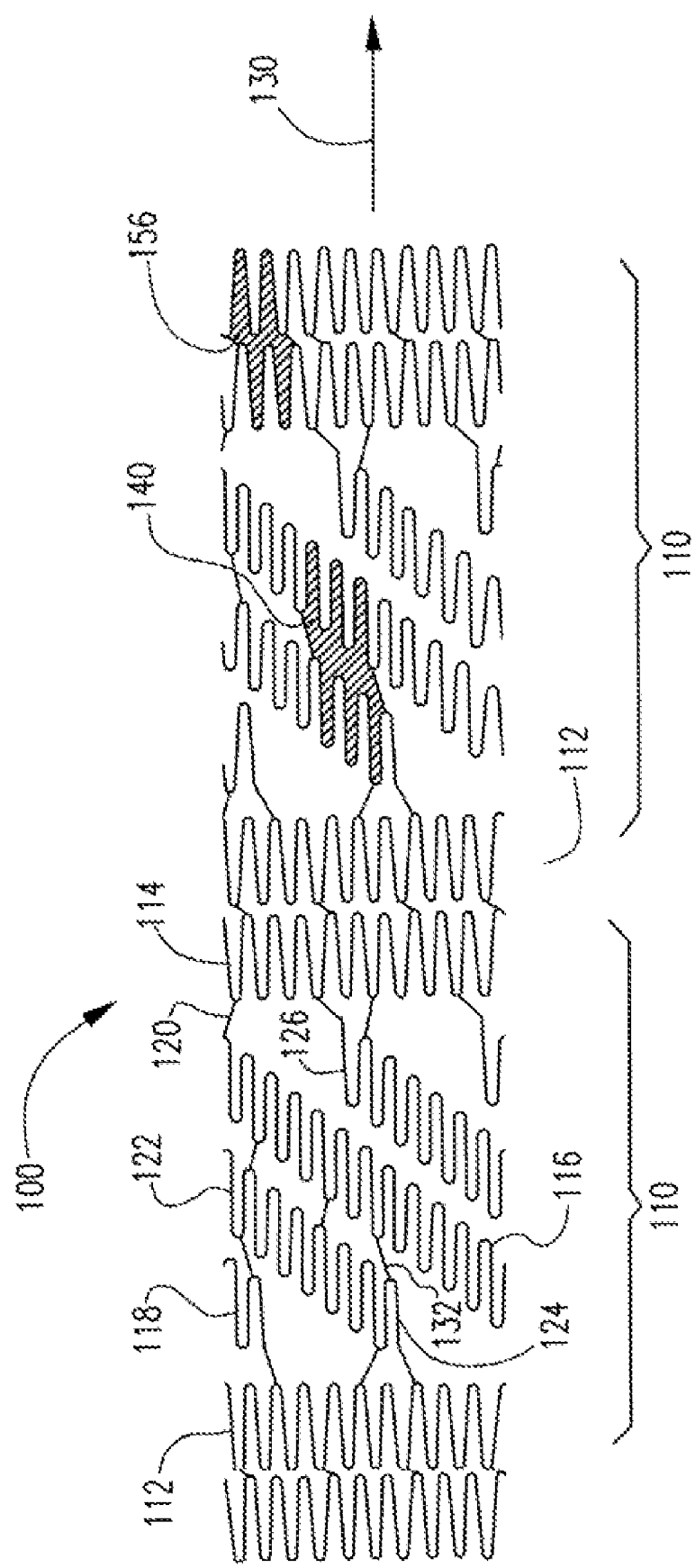
FIG. 11 is a flat pattern of an inventive stent.

The connectivity between the generally helical sections results in the presence of cells. As shown in FIGS. 2 and 11, for example, cell 140 is bounded at one end by one of the first and second generally helical sections and bounded at another end by another of the first and second generally helical sections. If connectors extend between the generally helical sections, then the connectors will form part of the sidewall of the cells. Furthermore, as shown in FIGS. 2 and 11, for example, the stent may optionally include cells 156 which are bounded at both ends by tubular, closed ring sections.

Figure 5B:
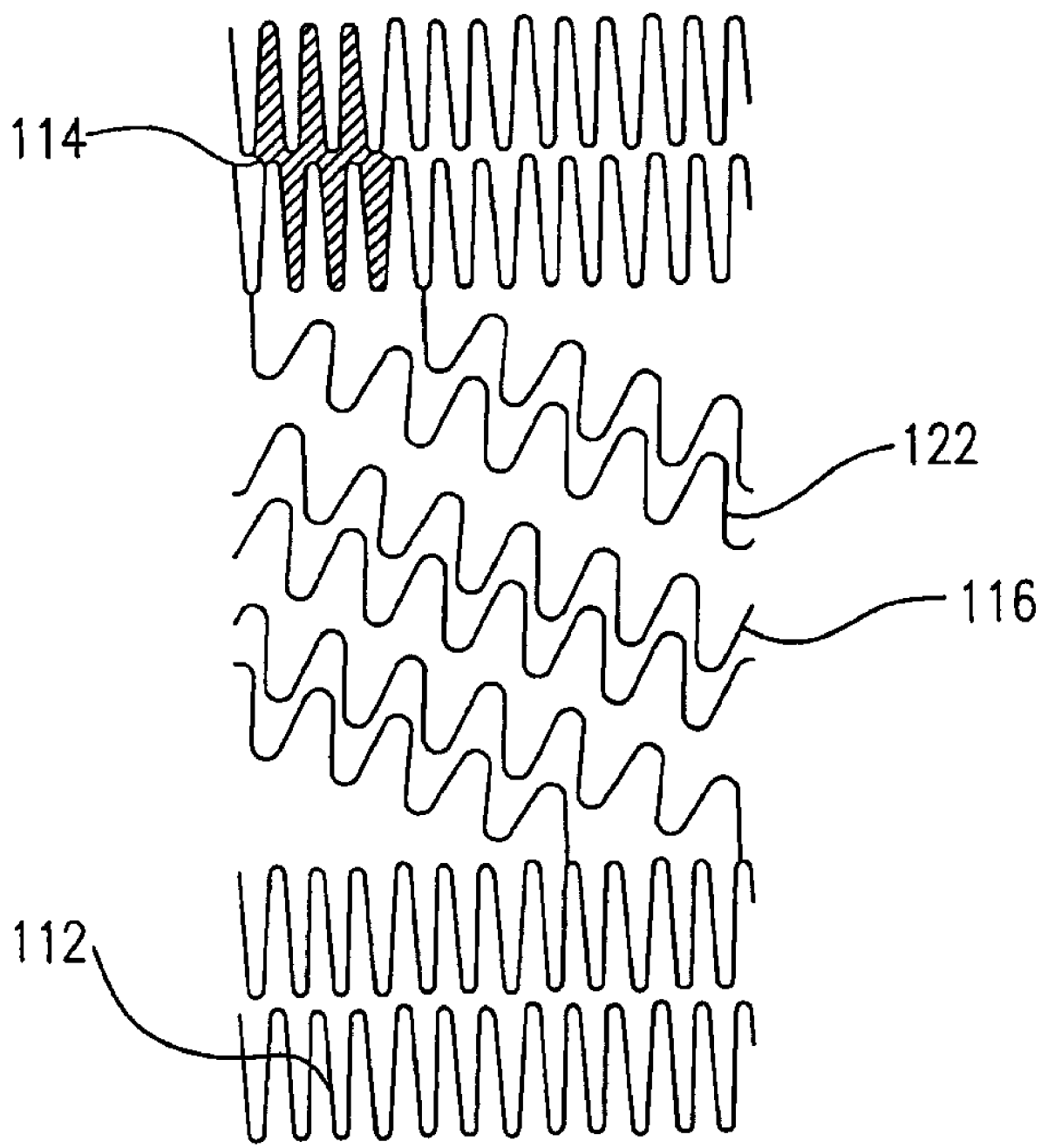
FIG. 5b shows an embodiment of an inventive stent with nesting generally helical sections.

It is also within the scope of the invention for one or more portions of one of the first and second generally helical sections to nest within one or more portions of the other of the first and second generally helical section. An example of such nesting is shown in FIG. 5b. First generally helical section 116 nests within second generally helical section 122.

Figure 5D:
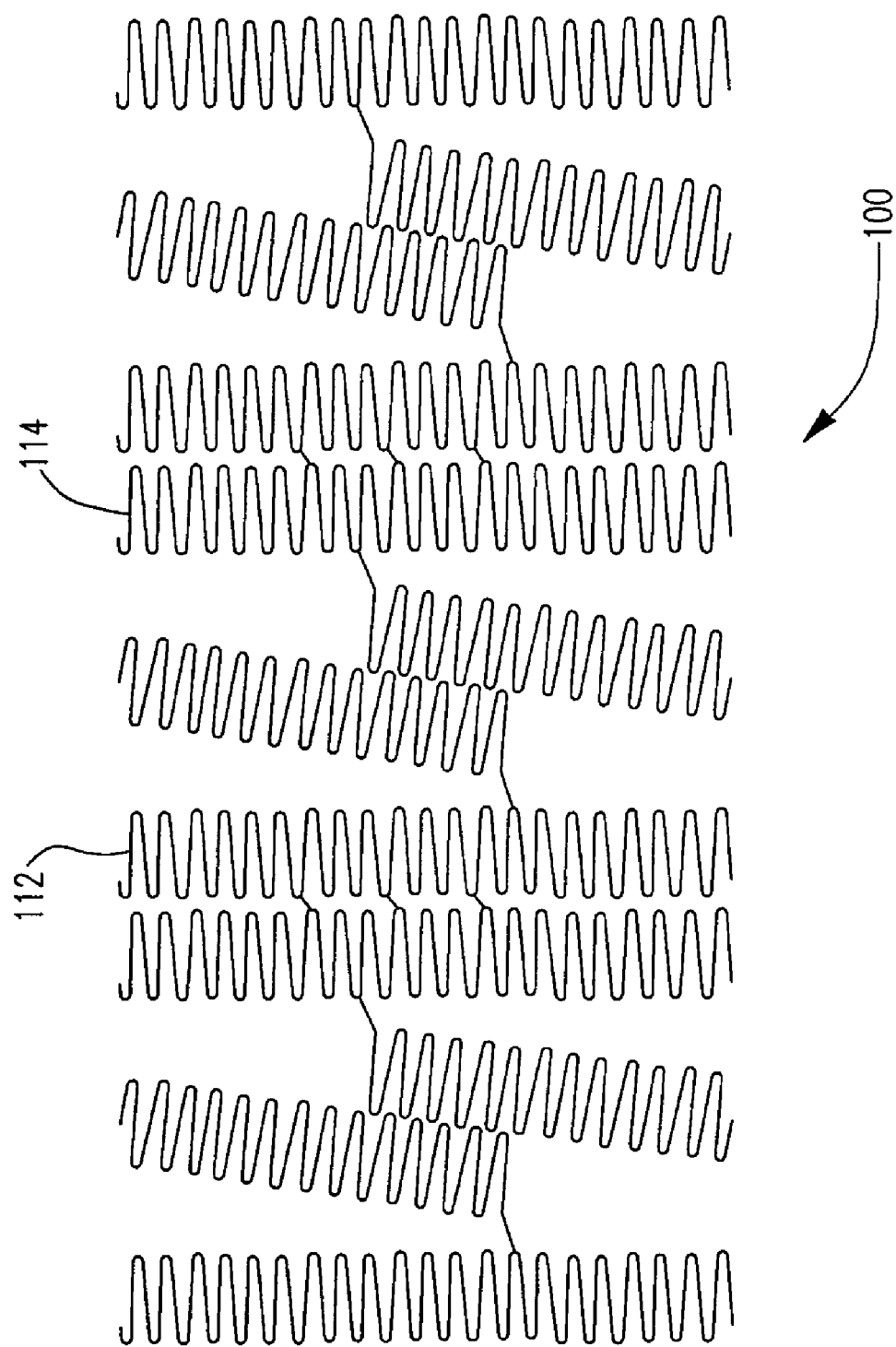
FIG. 5d shows an embodiment of an inventive stent with closed ring sections and nesting helical sections.

An example of a stent with one generally helical section 116, portions of which nest with one another is shown at 100 in FIG. 5c. The stent of FIG. 5c is shown with one generally helical section joining closed ring sections 112 and 114, each of which consists of a single closed serpentine ring. The single nesting overlapping generally helical segment may also be used in any of the other embodiments of the invention disclosed herein. To that end, the invention, in some embodiments, encompasses a stent having a plurality of closed ring sections, or non-helical ring, sections, which are interconnected by a generally helical connector, portions of the generally helical connector nesting within other portions of the generally helical connector. The closed ring sections, or non-helical ring sections may include one or more serpentine bands. An example of this is shown at 100 in FIG. 5d.

Figure 8:
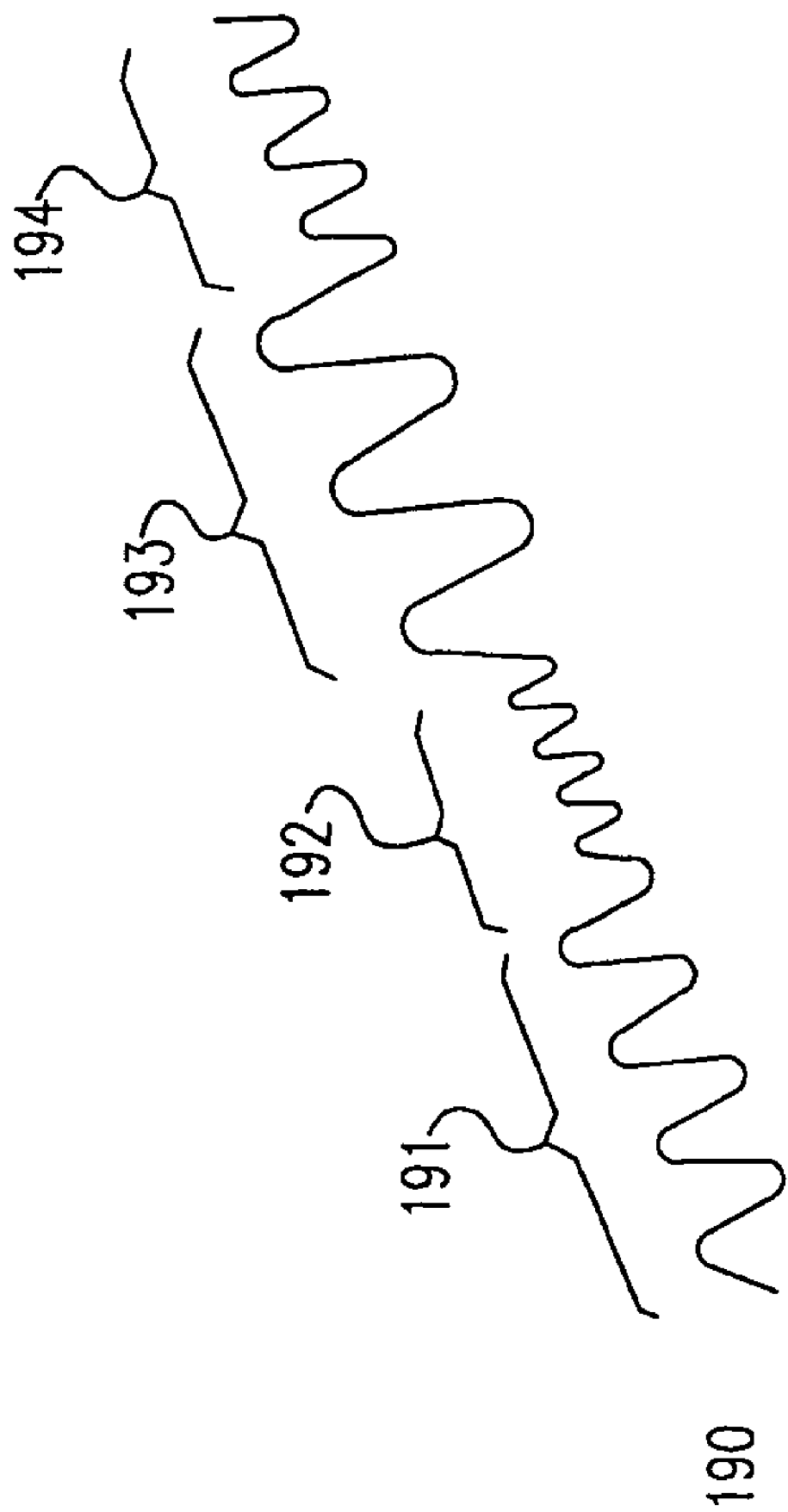
FIG. 8 is a flat pattern of generally helical section for use in the inventive stents.

As discussed above, the generally helical sections may have a uniform pitch or a non-uniform pitch. They may have an alternating pattern of longer and shorter struts, as shown by way of example in FIG. 2 where every other strut of the generally helical section is a longer strut. Other patterns of struts may also be used in the generally helical sections. For example, a generally helical section may include struts of three or more different lengths. A generally helical section may include portions which may be characterized by two or more different wavelengths or amplitudes or may include sections in which the spacing between adjacent peaks of the generally helical section varies. An example of a generally helical section which may be characterized as having multiple wavelengths is shown at 190 in FIG. 8. Generally helical section 190 includes 4 different portions 191-194 of different wavelengths and different amplitudes.

Figure 9:
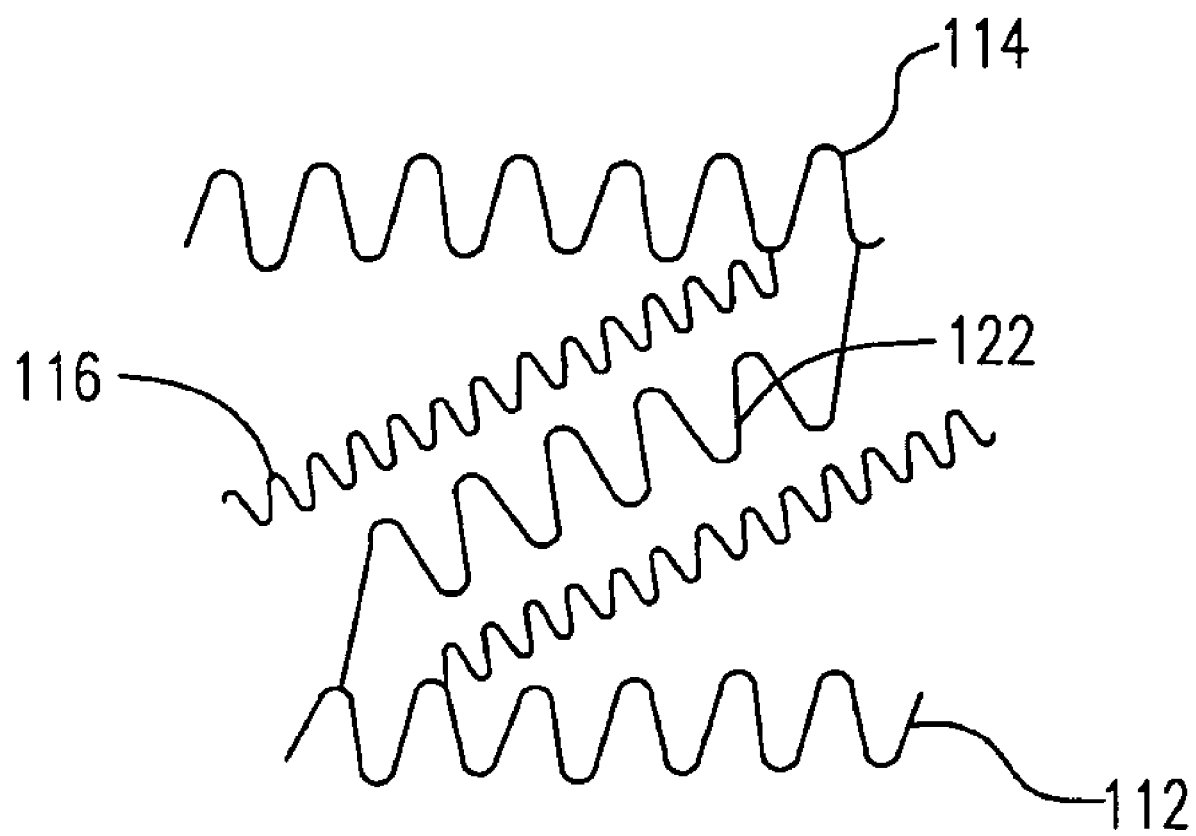
FIG. 9 is a flat pattern of an inventive stent segment illustrating first and second generally helical sections of different wavelengths and amplitudes.

Different generally helical sections may have struts of different lengths from one another and/or may be characterized as having different wavelengths from one another and/or different amplitudes from one another and/or may have different pitches. The generally helical sections may also span different numbers of degrees. An example of some of these features is shown in FIG. 9. First generally helical section 116 has a smaller amplitude and wavelength than second generally helical section 122. Also, first generally helical section 116 spans 720 degrees while second generally helical section 122 spans 360 degrees.

It is within the scope of the invention for the tubular closed ring sections to be in the form of a single serpentine closed ring or a plurality of interconnected closed serpentine rings. An example of the former is shown in FIG. 2. Where a plurality of serpentine bands form a closed ring section, the serpentine bands may all be of like geometry or may include different geometries. Where the geometries are the same, the serpentine bands may be in phase with one another or out of phase with one another.

It is also within the scope of the invention for a segment to have non-helical serpentine rings which are open in place of serpentine closed rings. A non-limiting example of such an embodiment is such at 100 in FIG. 6. Serpentine rings 212 and 214 are non-helical open serpentine rings in that they do not form a closed path around the longitudinal axis of the stent and are not generally helical. The stent of FIG. 6 is shown with two non-helical open serpentine bands. It is within the scope of the invention for any of the closed serpentine bands shown in any of the Figures to be replaced by non-helical open serpentine bands.

Figure 7:
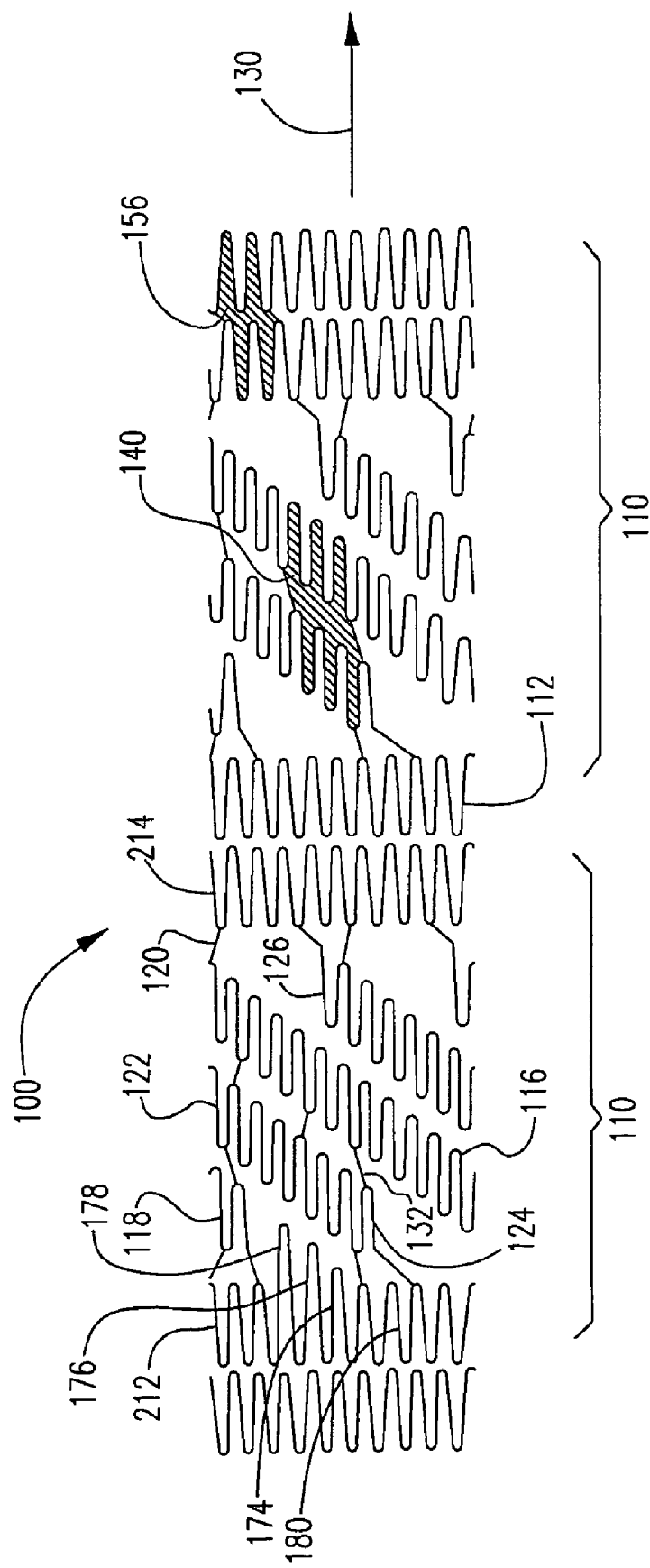
FIG. 7 is a flat pattern of an inventive stent.

In some embodiments, the serpentine closed rings and non-helical open serpentine rings may consist of interconnected struts of the same length. In other embodiments, the serpentine closed rings and non-helical open serpentine rings may include struts of different lengths. As shown by way of non-limiting example in FIG. 7, serpentine closed ring 112 includes struts 178, 176, 174 and 180 of different lengths, decreasing in length from the longest strut 178 to the shortest strut 180. Thus, serpentine closed ring 112 includes peaks which extend to different axial locations. The longer struts may be used in regions where there would otherwise be a large open space between the closed serpentine rings and the nearest generally helical section. FIG. 7 shows only one serpentine closed ring which has been provided with struts of different lengths. It is within the scope of the invention for all of the serpentine closed rings to be provided with struts of different lengths or for some, but not all, of the serpentine closed rings to be provided with such struts. Likewise, where non-helical serpentine open rings are used, the rings may be provided with different length struts within a ring.

Figure 10:
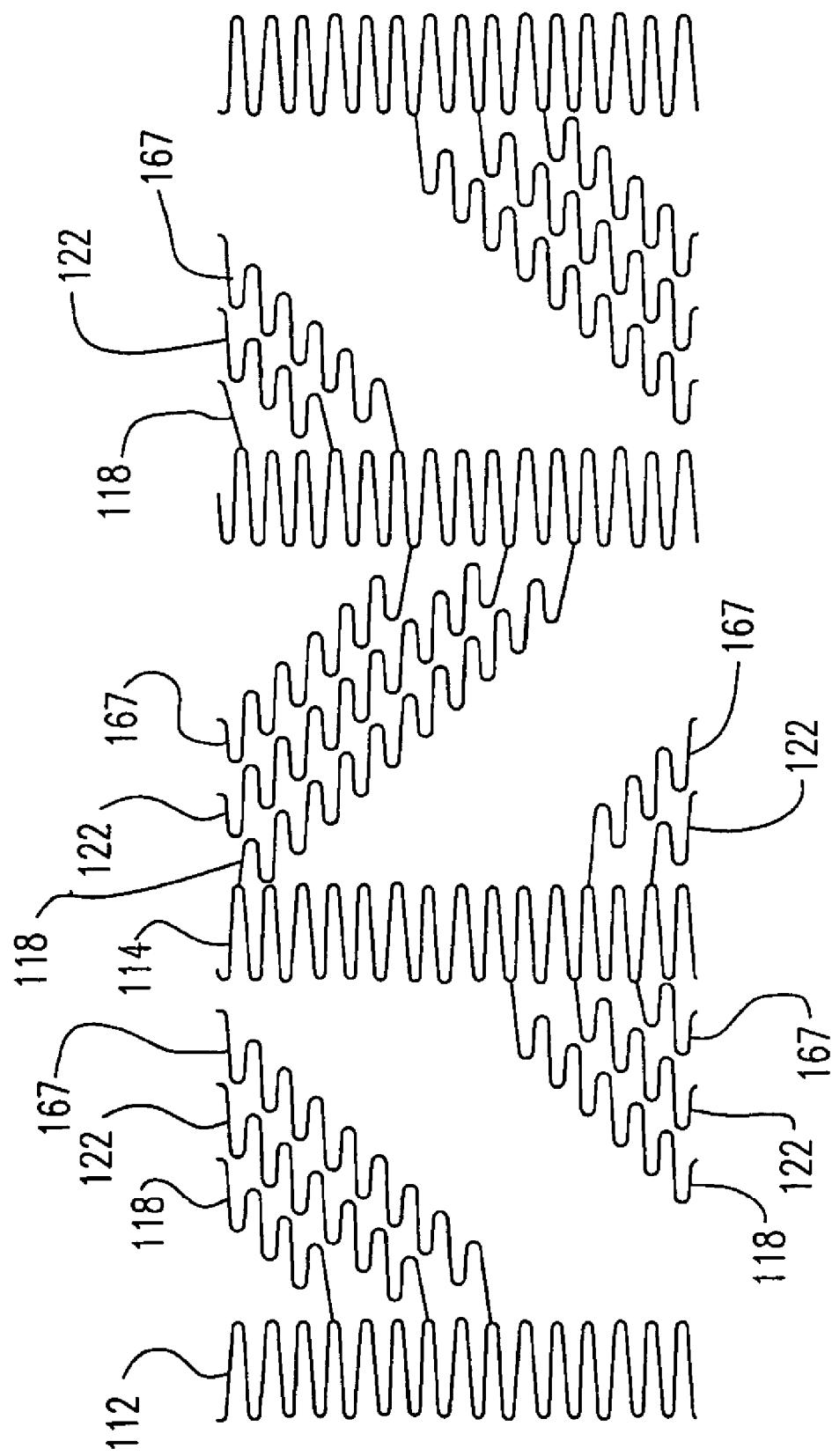
FIG. 10 is a flat pattern of an inventive stent.

The generally helical portions of the stents shown in FIGS. 2, 6 and 7 have two generally helical sections disposed side-by-side. Other embodiments of the invention may be made by modifying any of the stents disclosed herein to have a single generally helical section in place of the two side-by-side generally helical sections. Still other embodiments of the invention may have more than two side-by-side generally helical sections. Thus, it is within the scope of the invention for the stent to have three, four, five, six, seven or more side-by-side generally helical sections extending between serpentine closed rings or, more generally, between non-helical ring sections. Such a stent is shown by way of example in FIG. 10.

It is also within the scope of the invention for the generally helical sections to extend around the longitudinal axis of the stent for less than a complete turn (i.e. less than 360 degrees) or for one or more turns (i.e. 360 degrees, 720 degrees, 1080 degrees or more or fractions thereof).

The inventive stents may have only a single segment 110 or, as shown in FIGS. 2 and 11, may comprise a plurality of segments 110. Desirably, where a plurality of segments 110 are present, the segments will be arranged end-to-end, as shown in FIG. 11, for example, with adjacent segments connected one to another. Stents having two, three, four, five, six, seven, eight, nine, ten or more of such segments are within the scope of the invention.

The inventive stents may also be used in conjunction with graft material to provide a graft. The graft material may be disposed within the stent or outside the stent. The graft material may be coextensive with the stent or with only a portion of the stent. The graft material may extend all the way around the circumference of the stent or around only a portion of the stent.

The inventive stents disclosed herein may also be used as part of a stent having two or more branches. Examples of such stents include bifurcated stents.

The inventive stents disclosed herein may be tapered diameter or of uniform diameter in the expanded state. The taper may be uniform or non-uniform. The expanded stent may have two ends of a larger diameter than a middle section or only one end of larger diameter. The expanded stent may have a middle section of larger diameter than the ends of the stent. More generally, the expanded stent may have one or more portions of different diameter from other portions of the stent.

The inventive stents may have a constant wall thickness or a non-uniform wall thickness.

It is within the scope of the invention for the helical segment that is employed in the inventive stents disclosed herein to be attached to the ring section at a single location, as shown by way of example in FIG. 5*b*, or for the helical segment to be attached to the ring section at a plurality of locations, as shown by way of example in FIG. 5*a*. It is within the scope of the invention for each end of the helical segment to be attached at a single location to a ring segment. It is also within the scope of the invention for each end of the helical segment to be attached at a plurality of locations to a ring segment. It is further within the scope of the invention for one end of the helical segment to be attached at a plurality of locations to a ring segment and the another end of the helical segment to be attached to a ring segment at a single location.

The inventive stents may be made from any suitable biocompatible materials including one or more polymers, one or more metals or combinations of polymer(s) and metal(s). Examples of suitable materials include biodegradable materials that are also biocompatible. By biodegradable is meant that a material will undergo breakdown or decomposition into harmless compounds as part of a normal biological process. Suitable biodegradable materials include polylactic acid, polyglycolic acid (PGA), collagen or other connective proteins or natural materials, polycaprolactone, hylauric acid, adhesive proteins, co-polymers of these materials as well as composites and combinations thereof and combinations of other biodegradable polymers. Other polymers that may be used include polyester and polycarbonate copolymers. Example of suitable metals include, but are not limited to, stainless steel, titanium, tantalum, platinum, tungsten, gold and alloys of any of the above-mentioned metals. Examples of suitable alloys include platinum-iridium alloys, cobalt-chromium alloys including ELGIOY®, (a nickel cobalt chromium alloy also known as Phynox), MP35N alloy, nickel-titanium alloys, for example, Nitinol and nickel-titanium-platinum alloys.

The inventive stents may be made of shape memory materials such as superelastic Nitinol or spring steel, or may be made of materials which are plastically deformable. In the case of shape memory materials, the stent may be provided with a memorized shape and then deformed to a reduced diameter shape. The stent may restore itself to its memorized shape upon being heated to a transition temperature and having any restraints removed therefrom.

The inventive stents may be created by methods including cutting or etching a design from a tubular stock, from a flat sheet which is cut or etched and which is subsequently rolled or from one or more interwoven wires or braids. Any other suitable technique which is known in the art or which is subsequently developed may also be used to manufacture the inventive stents disclosed herein.

The invention is also directed to a delivery system such as a catheter with an inventive stent disclosed herein disposed on the delivery system. The delivery catheter may be a balloon catheter or may be a catheter designed for delivery of self-expanding stents.

Typically, the stent will be reduced in size and disposed about a deliver catheter. The reduction in size typically entails reducing in size the diameter of the stent. The reducing in size and disposing of the stent about the catheter may occur simultaneously or in a plurality of steps. By way of non-limiting examples, the stent may be reduced in size and then disposed about a catheter followed by further reduction of the stent in size; the stent may also be disposed about the catheter and then reduced in size, in one or more reduction steps. In the case of balloon expandable stents, the stent may be crimped onto the balloon. In the case of self-expanding expanding stents, the stents may be crimped so that they fit within a retractable sheath.

One or more embodiments of the inventive stents may be radially constrained by changing the wavelength or, more generally, the spacing between peaks of the serpentine bands and of the generally helical sections. The resulting decrease in size of the stent and subsequent expansion of the stent will occur with less twisting than would occur with a coil stent.

The stents disclosed herein may be used in any of the body lumens or vessels disclosed herein. At least some embodiments of the inventive stents may be of particular benefit when used in a superficial femoral artery (SFA) or in other regions where high axial and bending compliance is required.

The invention is also directed to methods of treatment of a bodily vessel using any of the inventive stents disclosed herein. In accordance with the method, a delivery system including a stent is inserted in a bodily vessel, including any of those disclosed herein. The stent is delivered to a desired bodily location and expanded via the use of a balloon, by withdrawing a restraining sheath or by any other suitable method. The delivery system is then removed from the body, with the stent remaining at the desired bodily location.

In some embodiments the stent, the delivery system or other portion of the assembly may include one or more areas, bands, coatings, members, etc. that is (are) detectable by imaging modalities such as X-Ray, MRI, ultrasound, etc. In some embodiments at least a portion of the stent and/or adjacent assembly is at least partially radiopaque.

In some embodiments the at least a portion of the stent is configured to include one or more mechanisms for the delivery of a therapeutic agent. Often the agent will be in the form of a coating or other layer (or layers) of material placed on a surface region of the stent, which is adapted to be released at the site of the stent's implantation or areas adjacent thereto.

A therapeutic agent may be a drug or other pharmaceutical product such as non-genetic agents, genetic agents, cellular material, etc. Some examples of suitable non-genetic therapeutic agents include but are not limited to: anti-thrombogenic agents such as heparin, heparin derivatives, vascular cell growth promoters, growth factor inhibitors, Paclitaxel, etc. Where an agent includes a genetic therapeutic agent, such a genetic agent may include but is not limited to: DNA, RNA and their respective derivatives and/or components; hedgehog proteins, etc. Where a therapeutic agent includes cellular material, the cellular material may include but is not limited to: cells of human origin and/or non-human origin as well as their respective components and/or derivatives thereof. Where the therapeutic agent includes a polymer agent, the polymer agent may be a polystyrene-polyisobutylene-polystyrene triblock copolymer (SIBS), polyethylene oxide, silicone rubber and/or any other suitable substrate.

The above disclosure is intended to be illustrative and not exhaustive. This description will suggest many variations and alternatives to one of ordinary skill in this art. The various elements shown in the individual figures and described above may be combined or modified for combination as desired. All these alternatives and variations are intended to be included within the scope of the claims where the term "comprising" means "including, but not limited to". Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

This completes the description of invention. Those skilled in the art may recognize other equivalents to the specific embodiment described herein which equivalents are intended to be encompassed by the claims attached hereto.

The invention claimed is:

1. A stent comprising:
a first non-helical ring section comprising at least one serpentine band having peaks and troughs and struts extending therebetween;
a second non-helical ring section comprising at least one serpentine band having peaks and troughs and struts extending therebetween;
a third non-helical ring section comprising at least one serpentine band having peaks and troughs and struts extending therebetween;
a first generally helical portion, the first generally helical portion including at least two side-by-side generally helical paths which extend in the same direction about the longitudinal axis of the stent, each of the at least two generally helical paths extending about a longitudinal axis of the stent for at least 360 degrees and having a first end, a second end, a plurality of peaks, and a plurality of troughs, the first ends of the at least two generally helical paths being directly engaged to the first non-helical ring section, the second ends of the at least two generally helical paths being directly engaged to the second non-helical ring section, the first non-helical ring section being adjacent to the second non-helical ring section; and
a second generally helical portion, the second generally helical portion including at least two side-by-side generally helical paths which extend in the same direction about the longitudinal axis of the stent, each of the at least two generally helical paths extending about the longitudinal axis of the stent for at least 360 degrees and having a first end and a second end, a plurality of peaks and a plurality of troughs, the first ends of the at least two generally helical paths being directly engaged to the second non-helical ring section, the second ends of the at least two generally helical paths being directly engaged to the third non-helical ring section, the second non-helical ring section being adjacent to the third non-helical ring section.

2. The stent of claim 1 wherein one or more of the non-helical rings sections are in the form of a closed ring section which forms a closed pathway around a longitudinal axis of the stent.

3. The stent of claim 1 wherein one or more of the non-helical ring sections are in the form of an open ring sections.

4. The stent of claim 1 wherein at least one non-helical ring section includes a serpentine band wherein at least some of the struts are of different length than others of the struts.

5. The stent of claim 1, the at least two side-by-side generally helical paths comprising a first generally helical path and a second generally helical path, at least a portion of the first generally helical path nesting within at least a portion of the second generally helical path.

* * * * *